(12) United States Patent
Auvray et al.

(10) Patent No.: US 11,000,250 B2
(45) Date of Patent: May 11, 2021

(54) VISUALIZING A COURSE OF A VASCULATURE STRUCTURE WITH AN OCCLUSION

(71) Applicant: KONINKLIJKE PHILIPS N.V., Eindhoven (NL)

(72) Inventors: Vincent Maurice Andre Auvray, Meuden (FR); Pierre Henri Lelong, Saint-Mande (FR); Raul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/474,777

(22) PCT Filed: Jan. 3, 2018

(86) PCT No.: PCT/EP2018/050150
§ 371 (c)(1),
(2) Date: Jun. 28, 2019

(87) PCT Pub. No.: WO2018/127520
PCT Pub. Date: Jul. 12, 2018

(65) Prior Publication Data
US 2019/0343474 A1    Nov. 14, 2019

(30) Foreign Application Priority Data
Jan. 5, 2017  (EP) .................................. 17305009

(51) Int. Cl.
*G06T 7/00*       (2017.01)
*A61B 6/00*       (2006.01)
*G06T 11/60*      (2006.01)

(52) U.S. Cl.
CPC .............. *A61B 6/504* (2013.01); *A61B 6/463* (2013.01); *A61B 6/481* (2013.01); *A61B 6/486* (2013.01);
(Continued)

(58) Field of Classification Search
CPC ......... A61B 6/504; A61B 6/463; A61B 6/481; A61B 6/486; A61B 6/5217; A61B 6/5288;
(Continued)

(56) References Cited

U.S. PATENT DOCUMENTS 8,781,193 B2    7/2014  Steinberg et al.
10,317,852 B1 *  6/2019  Spooner ................. F42B 15/10
(Continued)

FOREIGN PATENT DOCUMENTS

DE         102007046454 A1     12/2008
WO    WO-2006038166 A2 *   4/2006   .......... G06T 11/005
WO         2008051841 A1      5/2008

OTHER PUBLICATIONS

Aziz et al: "Chronic Total Occlusions—A Stiff Challenge Requiring a Major Breakthrough: Is There Light at the End of the Tunnel"; Heart, 2005, 91(Suppl 111), pp. 42-48.
(Continued)

*Primary Examiner* — Yi Wang

(57) ABSTRACT

The present invention relates to visualizing vasculature structure. In order to provide an improved visualizing a course of a vasculature structures with an occlusion, it is provided: a) to determine (102) a region of interest in a first image of a sequence of a cardiac vasculature structure, which is at least partly injected with contrast agent; wherein the vasculature structure comprises an occlusion and wherein vessel portions distal of the occlusion are non-visible; b) to identify (104) a trajectory proposal from a
(Continued)

proximal vessel portion that is visible in the image to a distal portion of the occlusion as a first estimation of the non-visible vessel portions; c) to modify (106) the trajectory proposal generating a plurality of possible trajectories for matching with the vessel course in a next image of the sequence; d) to determine (108) a plausibility value for each of the possible trajectories; e) to select (110) the possible trajectory with the highest plausibility value as vessel course indicator for the first image; f) to repeat (112) steps c) to e) for each image of the sequence to achieve a sequence of vessel course indicators; g) to associate (114) the vessel course indicators to the images corresponding to the same heart phase of the sequence of the cardiac vasculature structure; and h) to display (116) an illustration of the cardiac vasculature structure with the associated course indicators.

19 Claims, 8 Drawing Sheets

(52) U.S. Cl.
CPC .......... *A61B 6/5217* (2013.01); *A61B 6/5288* (2013.01); *G06T 7/0012* (2013.01); *G06T 11/60* (2013.01); *A61B 6/4441* (2013.01); *G06T 2207/10016* (2013.01); *G06T 2207/30048* (2013.01); *G06T 2207/30101* (2013.01)

(58) Field of Classification Search
CPC ..... A61B 6/4441; A61B 6/503; A61B 6/5211; A61B 6/487; A61B 6/465; G06T 7/0012; G06T 11/60; G06T 2207/10016; G06T 2207/30048; G06T 2207/30101; G16H 50/20

See application file for complete search history.

(56) References Cited

U.S. PATENT DOCUMENTS

| | | | |
|---|---|---|---|
| 2006/0122501 | A1 | 6/2006 | Lara-Montalvo et al. |
| 2008/0097200 | A1* | 4/2008 | Blume .................. A61B 6/481 600/431 |
| 2010/0296709 | A1* | 11/2010 | Ostrovsky-Berman ...................... G06T 7/11 382/128 |
| 2014/0088416 | A1* | 3/2014 | Sakuragi ................... G06T 7/12 600/425 |
| 2014/0369563 | A1 | 12/2014 | Kalevo et al. |

OTHER PUBLICATIONS

Frangi et al: "Multiscale Vessel Enhancement Filtering"; MIC-CAI'98, Lecture Notes in Computer Science. vol. 1496, 1998, pp. 130-137.
PCT/EP2018/050150, ISR & WO, Apr. 20, 2018, 14 Pages.
Rakshe et al: "Knowledge-Based Interpolation of Curves: Application to Femoropopliteal Arterial Centerline Restoration"; Med Image Anal, 2007, vol. 11(2), pp. 157-168.

\* cited by examiner

VISUALIZING A COURSE OF A VASCULATURE STRUCTURE WITH AN OCCLUSION

CROSS-REFERENCE TO PRIOR APPLICATIONS

This application is the U.S. National Phase application under 35 U.S.C. § 371 of International Application No. PCT/EP2018/050150, filed on Jan. 3, 2018, which claims the benefit of or European Patent Application No. 17305009.7, filed on Jan. 5, 2017. These applications are hereby incorporated by reference herein.

FIELD OF THE INVENTION

The present invention relates to visualizing vasculature structure, and in particular relates to a device and a method for visualizing a course of an occluded vasculature.

BACKGROUND OF THE INVENTION

As an example for the need to visualizing vasculature structures, it is referred to chronic total occlusion (CTO) as an intervention that can be performed percutaneously. When treating a CTO percutaneously, a clinician may steer his guide wire through the occluded region, inside a lumen that the clinician can actually not see. The occlusion needs to be pierced, while taking care to not derive subintimal, or even rupture the vessel. US 2008/0097200 A1 describes a method of finding the location of an occluded portion of a blood vessel. However, it has been shown that a demand for an increasing quality of accuracy of the provided information exists.

SUMMARY OF THE INVENTION

There may thus be a need to provide an improved visualizing of a vasculature structures with an occlusion.

The object of the present invention is solved by the subject-matter of the independent claims; further embodiments are incorporated in the dependent claims. It should be noted that the following described aspects of the invention apply also for the device for visualizing an occluded vasculature and for the method for visualizing an occluded vasculature.

According to the present invention, a device for visualizing a course of an occluded vasculature is provided. The device comprises an image data supply unit, a determination unit, a processing unit and a display unit.

The image data supply unit is configured to provide a sequence of images of a cardiac vasculature structure, which is at least partly injected with contrast agent.

The determination unit is configured to determine a region of interest in a first image of the sequence of a cardiac vasculature structure.

The processing unit is configured to identify, in the region of interest, a trajectory proposal from a first visible vessel portion proximal to a non-visible vessel portion to a second visible vessel portion distal to the non-visible vessel portion of the occlusion, and to modify the trajectory proposal generating a plurality of possible trajectories for matching with a vessel course of the non-visible vessel portion, and to determine a plausibility value for at least one of the possible trajectories; and to select a possible trajectory for the vessel course based on the plausibility value of the trajectory.

Optionally, the modification, the determination and the selection can be repeated for different images of the sequence to achieve a sequence of vessel course indicators; and to associate the vessel course indicators to the images corresponding to the same heart phase of the sequence of the cardiac vasculature structure. For example, vessel course indicators may be determined at least for each image of a sequence of images covering an entire heart cycle.

The display unit is configured to display an indication of the selected trajectory as the vessel course of the non-visible vessel portion in the cardiac vasculature structure. Thus, in the original image, an indicator for the course of the non-visible vessel portion, e.g. an occlusion, may be shown. For example, an indicator is shown representing the most likely vessel course, or several indicators may be shown representing vessel courses corresponding to possible trajectories for which the plausibility value exceeds a predetermined threshold.

According to an example, for the determination unit, a user interface is provided configured to provide manual identification or modification of image data.

According to the present invention, also a method for visualizing a course of an occluded vasculature is provided. The method comprises the following steps:

a) determining a region of interest in a first image of a sequence of a cardiac vasculature structure, which is at least partly injected with contrast agent;

b) identifying, in the region of interest, a trajectory proposal from a first visible vessel portion proximal to a non-visible vessel portion to a second visible vessel portion distal to the non-visible vessel portion;

c) modifying the trajectory proposal generating a plurality of possible trajectories for matching with a vessel course of the non-visible vessel portion;

d) determining a plausibility value for at least one of the possible trajectories;

e) selecting a possible trajectory for the vessel course based on the plausibility value of the trajectory;

h) indicating the selected trajectory as the vessel course of the non-visible vessel portion in the cardiac vasculature structure.

In an embodiment, the method further comprises f) repeating steps c) to e) for each image of the sequence to achieve a sequence of vessel course indicators;

g) associating the vessel course indicators to the images corresponding to the same heart phase of the sequence of the cardiac vasculature structure.

According to an example, in step a), a vessel branch distal to an occlusion is determined automatically. Preferably, vessels are detected that stop abruptly.

According to an example, in step b), the trajectory is manually identified by a user via an interface.

According to an example, in step b), the trajectory is identified automatically.

According to an example, for step c), several prolongations of the vessel at the non-visible vessel portion are provided as trajectory proposals.

Further, in step d), a score may be provided for each prolongation based on at least one of the group of contrast for the potential distal vascular structure met by the prolongation, and smoothness of their connection at the proximal and distal parts, and anatomic probability for each prolongation, and similarity of successive trajectories. In an example, the prolongation with the best score is selected for step e).

According to an example, in step c), following step b) it is provided to generate anatomically plausible variations.

According to an example, step d) comprises at least one of the following sub-steps:

d1) associating a connection score to each of the possible trajectories based on a smoothness degree of the trajectory with visible portions of the vessel;
d2) associating an anatomical plausibility score to each of the possible trajectories based on a matching degree with an anatomical model of the vascular structure;
d3) associating an anatomical probability score based on a degree of variation of the possible trajectories with the selected trajectory for the previous image of the sequence;
d4) associating a matching score based on a degree of similarity with a number of vessel centerlines provided by a database; and
d5) associating a smoothness score based on a touching angle of the possible trajectories with a visible distal portion.

According to an example, in step e), a trajectory is selected for each heart phase.

According to an aspect, in examples, the vessel part corresponding to an occlusion can be made partially visible by means of an indication of the selected trajectory as a likely vessel course.

The clinician no longer needs to guess the course of the vessel in the occlusion by spatially interpolating between the injected vessels proximal and distal to the occlusion. Since a clinician no longer has to mentally perform a temporal interpolation to translate the imagined vessel course in time, support for the clinician is provided by the present invention.

Since the display omits the need for the clinician to mentally re-project the interpolation over the existing angiograms/roadmaps, the needs to reactivate memory from time to time by injecting contrast agent is also reduced.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
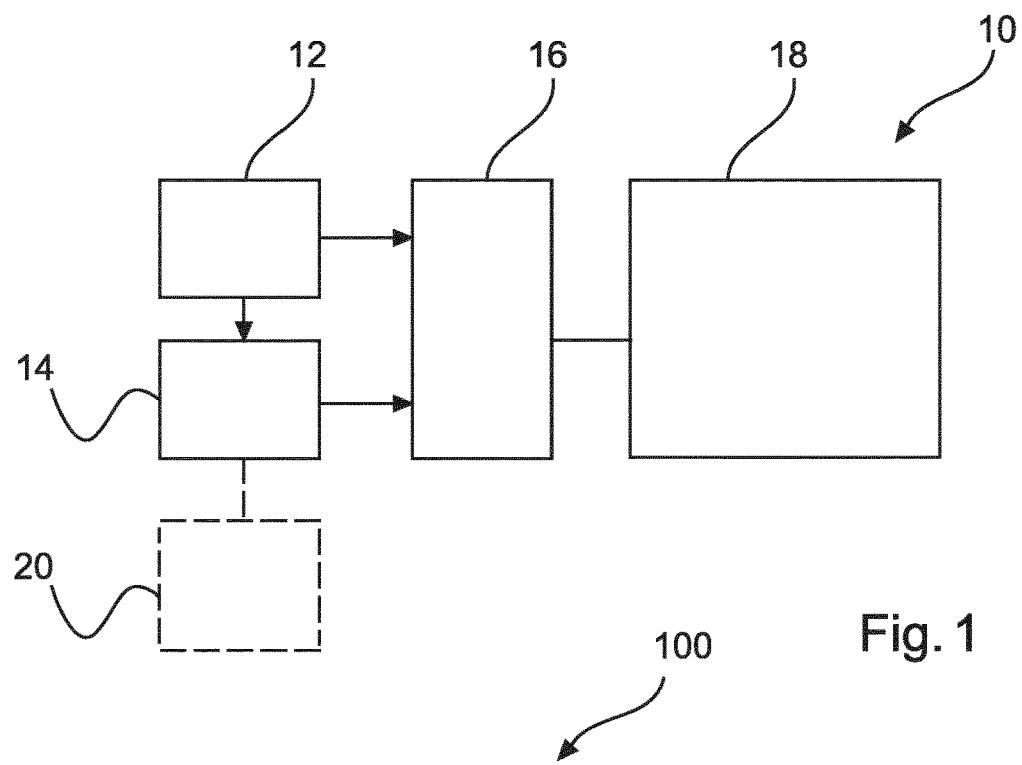
FIG. 1 shows an example of a device for visualizing an occluded vasculature.

FIG. 1 shows a device 10 for visualizing a course of an occluded vasculature. The device comprises an image data supply unit 12, a determination unit 14, a processing unit 16 and a display unit 18. The image data supply unit 12 is configured to provide a sequence of images of a cardiac vasculature structure, which is at least partly injected with contrast agent. In an example, the vasculature structure comprises an occlusion as a non-visible vessel portion.

The determination unit 14 is configured to determine a region of interest in a first image of the sequence of a cardiac vasculature structure. The processing unit 16 is configured to identify, in the region of interest, a trajectory proposal from a first visible vessel portion proximal to a non-visible vessel portion to a second visible vessel portion distal to the non-visible vessel portion of the occlusion. The processing unit 16 is also configured to modify the trajectory proposal generating a plurality of possible trajectories for matching with a vessel course of the non-visible vessel portion. The processing unit 16 is still further configured to determine a plausibility value for at least one of the possible trajectories. The processing unit 16 is further configured to select a possible trajectory for the vessel course based on the plausibility value of the trajectory.

The display unit 18 is configured to display an indication of the selected trajectory as the vessel course of the non-visible vessel portion in the cardiac vasculature structure.

In an example, the processing unit 16 is still further configured to repeat the modification, the determination and the selection for each image of the sequence to achieve a sequence of vessel course indicators. The processing unit 16 is furthermore configured to associate the vessel course indicators to the images corresponding to the same heart phase of the sequence of the cardiac vasculature structure.

In an example, the determination unit is part of the processing unit and the determination takes place automatically. In another example, the determination unit is a separate unit and the determination takes place manually by the user.

As an option (indicated with dotted lines), for the determination unit, a user interface 20 is provided configured to provide manual identification or modification of image data.

Figure 2:
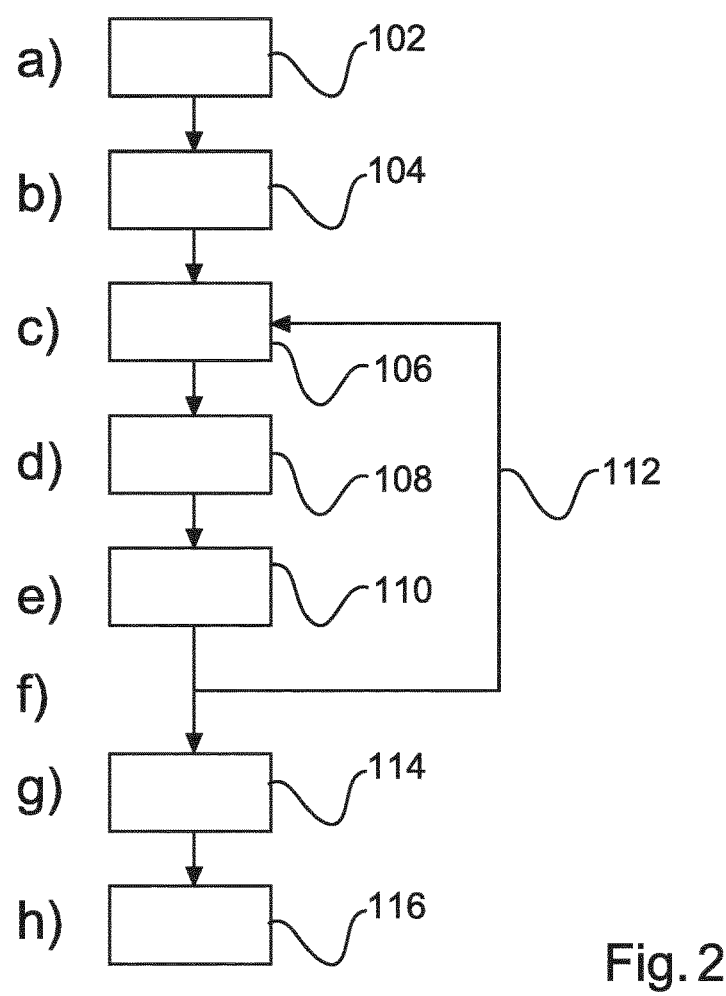
FIG. 2 shows an example of a method for visualizing an occluded vasculature.

FIG. 2 shows a method 100 for visualizing a course of an occluded vasculature. The method comprises the following steps: In a first step 102, also referred to as step a), a region of interest is determined in a first image of a sequence of a cardiac vasculature structure, which is at least partly injected with contrast agent; wherein the vasculature structure comprises an occlusion and wherein vessel portions distal of the occlusion are non-visible.

In a second step 104, also referred to as step b), in the region of interest, a trajectory proposal from a first visible vessel portion proximal to a non-visible vessel portion to a second visible vessel portion distal to the non-visible vessel portion is identified.

In a third step 106, also referred to as step c), the trajectory proposal is modified generating a plurality of possible trajectories for matching with a vessel course of the non-visible vessel portion.

In a fourth step 108, also referred to as step d), a plausibility value is determined for at least one of the possible trajectories.

In a fifth step 110, also referred to as step e), a possible trajectory is selected as vessel course indicator for the first image, based on the plausibility value. For example, the trajectory having the highest plausibility value is selected for the vessel course indicator. Alternatively, one or more trajectories having a plausibility value above a threshold are selected.

In an optional sixth step 112, also referred to as step f), the steps c) to e) are repeated, as indicated with a loop arrow, for each image of the sequence to achieve a sequence of vessel course indicators.

In an optional seventh step 114, also referred to as step g), the sequence of vessel course indicators from step f) are associated to the images corresponding to the same heart phase of the sequence of the cardiac vasculature structure.

In a final step 116, also referred to as step h), an illustration of the cardiac vasculature structure is displayed with the associated course indicators.

The illustration is provided as a guide or map for an occlusion treatment procedure.

In an example, in step h), a displayed image sequence provides augmented cardiac roadmapping, i.e. the displayed image sequence provides improved information about the vascular structure despite the occlusion that effects the visualization with contrast agent. The image sequence, for instance, may cover an entire cardiac cycle. For each phase of the heart cycle, an augmented roadmapping image including an indication of the vessel course of the non-visible vessel portion may be provided.

In an example, the course indicators are displayed in addition to a graphical indicator of the cardiac vasculature structure.

In an example, the course indicators are displayed in addition to existing images, e.g. directly overlaid on the images.

For example, a roadmap is provided based on subtraction angiography, and the course indicators are overlaid on the roadmap.

As an option, the course indicators are displayed with and without images or illustration of the vascular structure, i.e. the vasculature. In an example, the user is provided with an interface to switch between different modes of display.

In an example, the sequence relates to images of a heart sequence cycle.

In a further example, not shown in detail, in step a), a vessel branch distal to an occlusion is determined automatically. Preferably, vessels are detected that stop abruptly.

In a still further example, not shown in detail, in step b), the trajectory is manually identified by a user via an interface.

For example, in step b), the trajectory is identified automatically.

In an example, a large set of prolongations is generated and tested, and the most likely prolongation(s) (according to preset criteria such as smoothness of connection etc.) is(are) selected.

For example, one selected trajectory is then displayed.

In an example, a series of prolongations is provided, i.e. generated, and then subject to test criteria for further selection. In another example, a series of prolongations is provided, i.e. generated, within a predetermined field based on learned selections, and the prolongations are then subject to test criteria for further selection.

In another example, not shown in detail, in step b), the occlusion is determined, wherein the distal portion is visible. A prolongation of the vessel at the occlusion is identified as a trajectory proposal.

In an example, the occlusion is determined automatically. In another example, the occlusion is determined manually.

In a further example, not shown in detail, for step c), several prolongations are provided. And in step d), a score is provided for each prolongation based on at least one of the group of:

contrast for the potential distal vascular structure met by the prolongation;

proximal contrast, e.g. if test trajectories are not exactly arising from the stump, i.e. the vessel portion that is still visible, followed by the occlusion;

smoothness of their connection at the proximal and distal parts;

anatomic probability for each prolongation;

similarity of successive trajectories; and wherein the prolongation with the best score is selected for step g).

In an example, the score is provided, i.e. determined, automatically.

In an example, not further shown, following step b), it is provided to refine the trajectory proposal input by a user in order to correct for input inaccuracy. Further, the refinement includes smoothening the connecting parts of the trajectory proposal where a connecting with visible vessel portions is provided.

In a further first option, referred to as case 1, the determination steps are provided in an automatic manner. A large range of regular prolongations arising from the stump is selected, and the best one following a criterion as the one detailed above is selected.

In a further second option, referred to as case 2, the user draws a draft course. From this input, a series of trajectories (slight rotations, translations, skewings . . . ) is generated and the best one is selected.

In an example, in step b), the distal portion is visible in the image.

For example, for the determination of the initial trajectory in step b), basically a sizable set of "candidate" trajectories is generated, and each of their quality is evaluated (for example with a composite criterion that includes contrast of the vessels distally and proximally, smoothness of the connection, and anatomical plausibility of the trajectory shape), and the best is selected.

For example, in step c), following step b) it is provided to generate anatomically plausible variations.

In an example, not shown in detail, step d) comprises at least one of the following sub-steps:

d1) associating a connection score to each of the possible trajectories based on a smoothness degree of the trajectory with visible portions of the vessel;

d2) associating an anatomical plausibility score to each of the possible trajectories based on a matching degree with an anatomical model of the vascular structure;

d3) associating an anatomical probability score based on a degree of variation of the possible trajectories with the selected trajectory for the previous image of the sequence;

d4) associating a matching score based on a degree of similarity with a number of vessel centerlines provided by a database; and d5) associating a smoothness score based on a touching angle of the possible trajectories with a visible distal portion.

The anatomical plausibility is also referred to as anatomical likelihood.

In an example, in step e), a trajectory is selected for each heart phase. Step e), in one example, comprises a sub-step e1) of manually modifying the possible trajectory by the user via an interface.

In an example, in step g), a global transformation is provided to model the motion that is compensated for.

For example, a transformation is provided in order to show the heart at the same position. As an example, motion due to moving of the heart or due to breathing is thus compensated.

Figure 3:
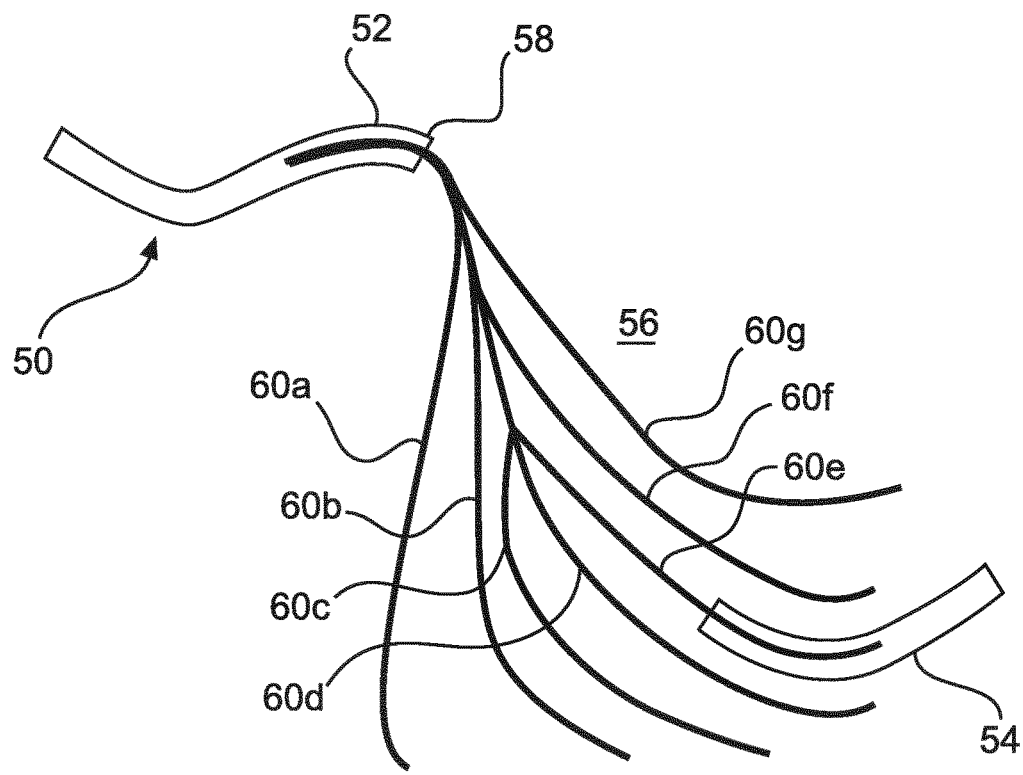
FIG. 3 shows an example of providing prolongations to determine a vessel branch distal to an occlusion.

FIG. 3 shows an example of part of an angiogram of a vascular structure 50 with a first vessel part 52 filled with contrast agent, and thus visible. Further, a second vessel part 54 is also visible due to also being filled with contrast agent. A region 56 between may comprise a vessel portion that is not visible in the angiogram, such as an occlusion in the vasculature. For example, it may be seen in the angiogram that a distribution of contrast agent abruptly stops at an "end" 58 of the first vessel part 52, also referred to as a "proximal" vessel part herein, being located proximal to the non-visible vessel portion. Similarly, the second vessel part 54 is also referred to as a "distal" vessel part herein, being located distal to the non-visible vessel portion.

A distal part of the vasculature may indirectly be fed by collaterals originating from other (non-occluded) branches of the vasculature. These branches can be part of the treated vascular tree, or of the other coronary tree (i.e. right if the CTO is in the left tree, and vice-versa), in which case a bilateral injection of contrast agent would be necessary. The second vessel portion, i.e. the vessel branch distal to the occlusion, may therefore only appear in a limited number of images, for example the end of an angiographic sequence.

A plurality of trajectory variations 60a, 60b, 60c, 60d, 60e, 60f and 60g are provided starting from the end 58 of the first vessel part 52. In this example, the trajectory variations may be regarded as prolongations of the first vessel part 52.

Whereas the figure shown all trajectory variations as solid black lines, in practice, for example, the anatomically more likely can be provided color coded with those variations in green that are anatomically more likely, such as the variation 60e, and those variations that are anatomically less likely in red, for example variations 60a and 60g. Other colors such as orange and light green or yellow can be provided for the other variations.

Figure 4:
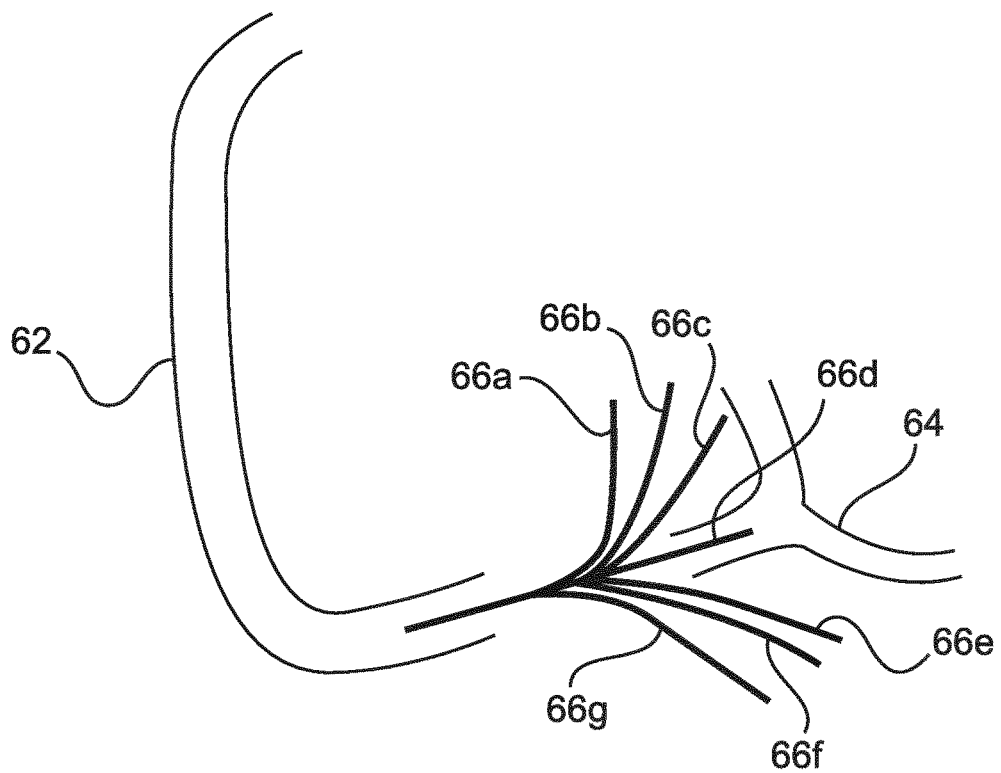
FIG. 4 shows another example of determining a vessel branch distal to an occlusion.

FIG. 4 shows another example of the interpolation process. A first part 62 of a vessel is shown in the angiogram, together with a second part 64. In between, i.e. where an occlusion may prevent blood flow, variations 66 are shown as a result from an interpolation process. For example, proposed interpolations 66d are anatomically more likely and are thus shown, for example, in green. Other proposed interpolations 66a and 66g are anatomically less likely and are thus shown in red. Further proposed interpolations are shown in orange (66b, 66f) and light green or yellow (66c, 66e).

Figure 5:
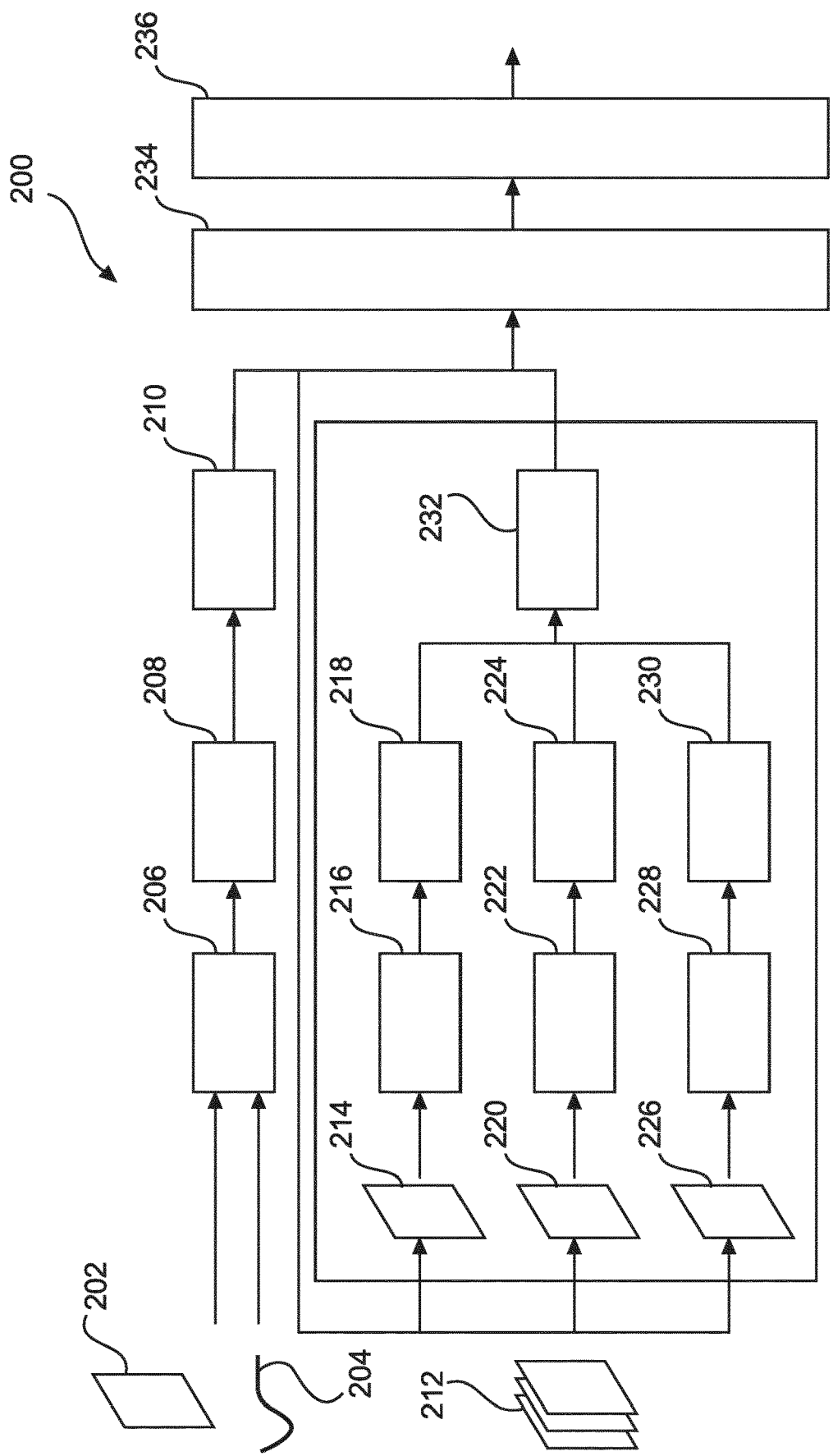
FIG. 5 shows steps of an example of a framework of steps for visualizing an occluded vasculature.

FIG. 5 shows an example of a method 200 for visualizing an occluded vasculature. As a first step, a selected angio (angiography) image 202 is provided. In addition, a vessel course 204 is provided by a user, such as drawn by a clinician. Next, at least one variation 206 is provided. Further, an evaluation 208 of the trajectory quality with the distal part is provided. The trajectory quality may relate to such criteria as the connection, but also other criteria listed above, such as contrast, anatomy likelihood, smoothness of the connection and the like. Then, a selection 210 of the best trajectory is provided. In parallel, a complete angio sequence 212 is provided.

In an embodiment, for each successive heart phase A, selection, variation and evaluation are provided. A first angio image (angio image A #1) acquired at a first heart phase is selected 214 and at least one variation of the trajectory is generated 216 and an evaluation 218 of its quality is provided. Further, a second angio image (angio image A #2) may be selected 220 at a second heart phase and at least one variation of the trajectory is generated 222 and an evaluation 224 of its quality is provided. Still further, additional (nth) angio image(s) (angio image A #n) may be selected 226 at different heart phases and at least one variation of the trajectory is generated 228 and an evaluation 230 of its quality is provided. In a selection step 323 a selection of the best trajectory is provided, based on the 1 to n evaluation. Following, the result of the selection 210 and the selection 232 are then provided to a quality threshold step 234, followed by a translation 236 to a complete sequence, which is then subject to display (not shown).

Figure 6:
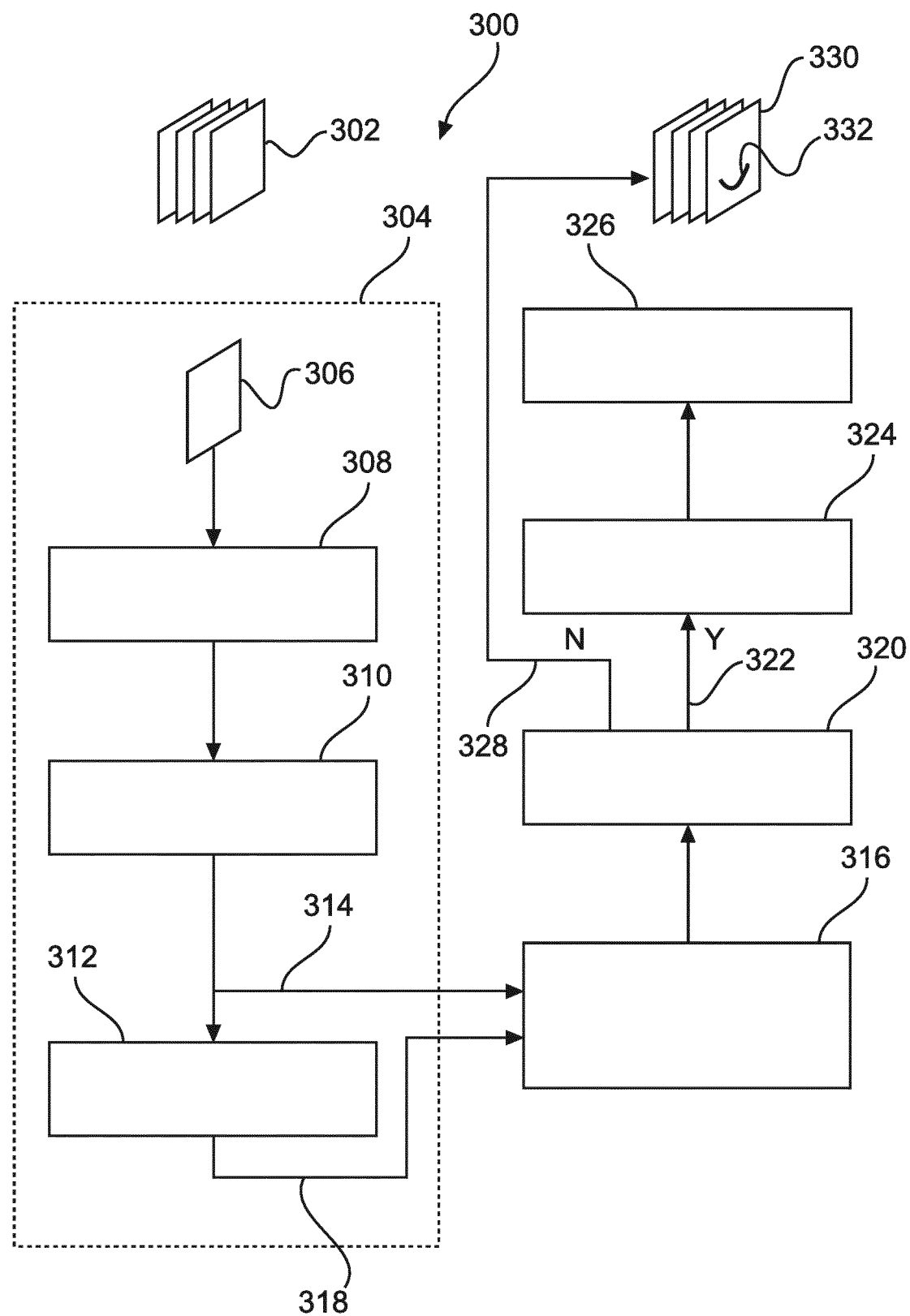
FIG. 6 shows steps of another example of a framework of steps for visualizing an occluded vasculature.

FIG. 6 shows an example of a method 300 for visualizing an occluded vasculature. Angiographic images 302 are provided. Then a frame by frame processing 304 takes place, as indicated by a dotted frame. Starting from an angiographic image 306, an identification 308 of a vessel branch proximal to occlusion is provided. Admissible vessel courses are generated 310, e.g. originating from identified vessel branches proximal to the occlusion. Next, trajectory quality evaluation takes place; for example, potentially met distal vessel branches are evaluated 321, e.g. based on existence, contrast and quality of the connection. Vessel courses, and anatomical likelihoods are also served 314 to a further step 318 of temporal optimization, in addition to providing 316 trajectory quality evaluation. The temporal optimization comprises selection of the most informative heart cycle, and of the corresponding most probably vessel courses. Also, a computation of an associated quality may be provided. As a result, selected heart cycle with most probable vessel courses in the occlusion, and associated quality is provided to a step 320 of threshold on quality. It is checked whether enough distal information is available to propose sensible vessel courses in the occlusion. In case of a positive result 322 ("YES"), a transfer 324 to the complete sequence is performed, including frames were the distal injection is invisible; followed by a possibility 326 of manual user edition. A sequence or roadmap 330 with proposed vessel-courses 332 in the occlusion is displayed if the quality is sufficient. In case of a negative result 328 ("NO"), the prolongations may be discarded, and the clinician is provided with a roadmap without prolongations, in order to avoid misleading trajectories.

Figure 7:
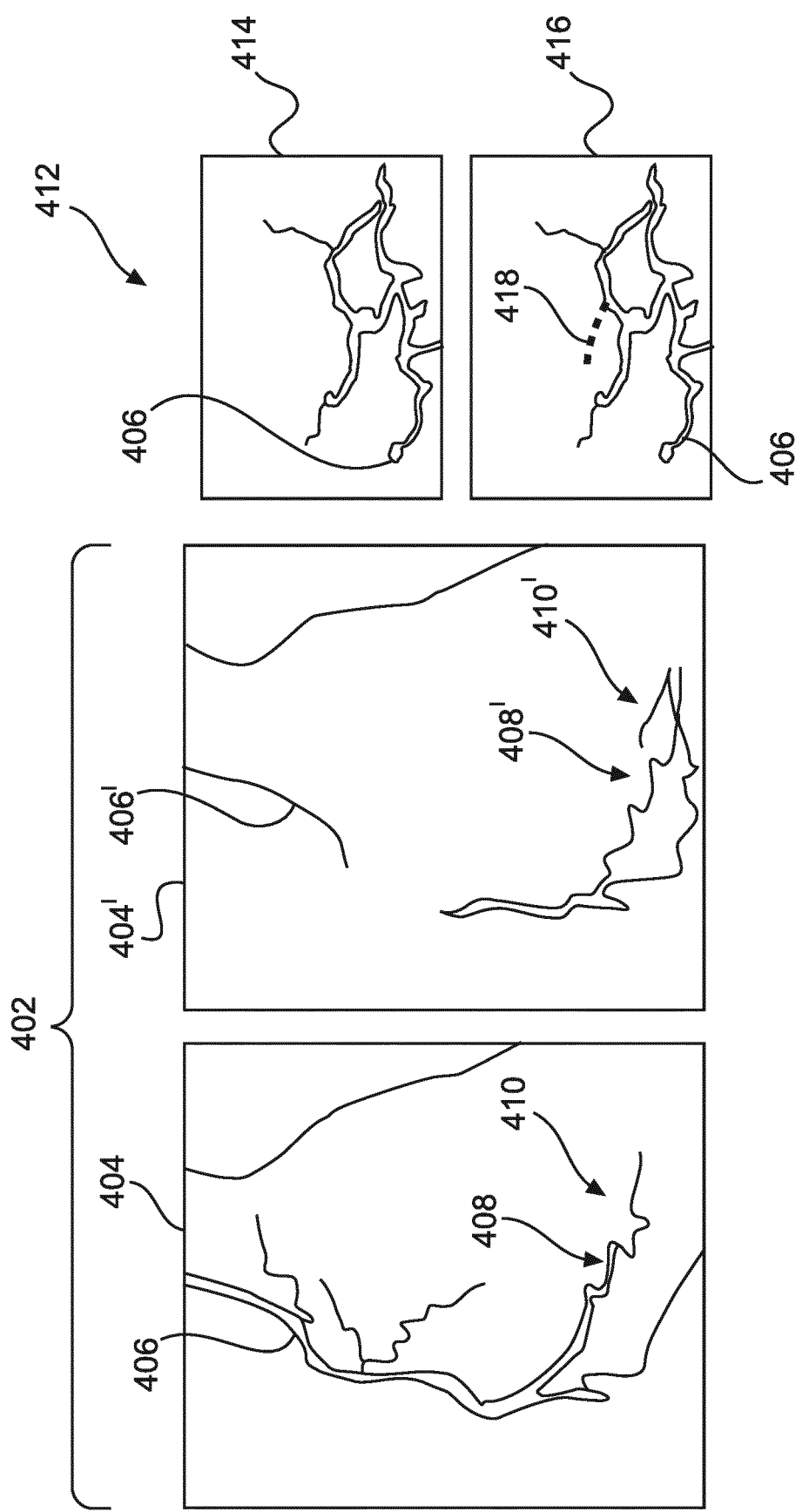
FIG. 7 shows angiograms of an example of a vascular structure with an occlusion and an indicated vessel course.

FIG. 7 relates to a first example of an occluded vessel. In a left part 402, two angiograms 404, 404' are shown with a first vascular structure 406, 406' having an occlusion 408, 408' where a distal part 410, 410' is faintly visible. In a right part 412, an upper image 414 shows an enlarged detailed view of the vascular structure 406', and a lower part 416 shows the detailed view with an interpolated vessel course 418.

Figure 8:
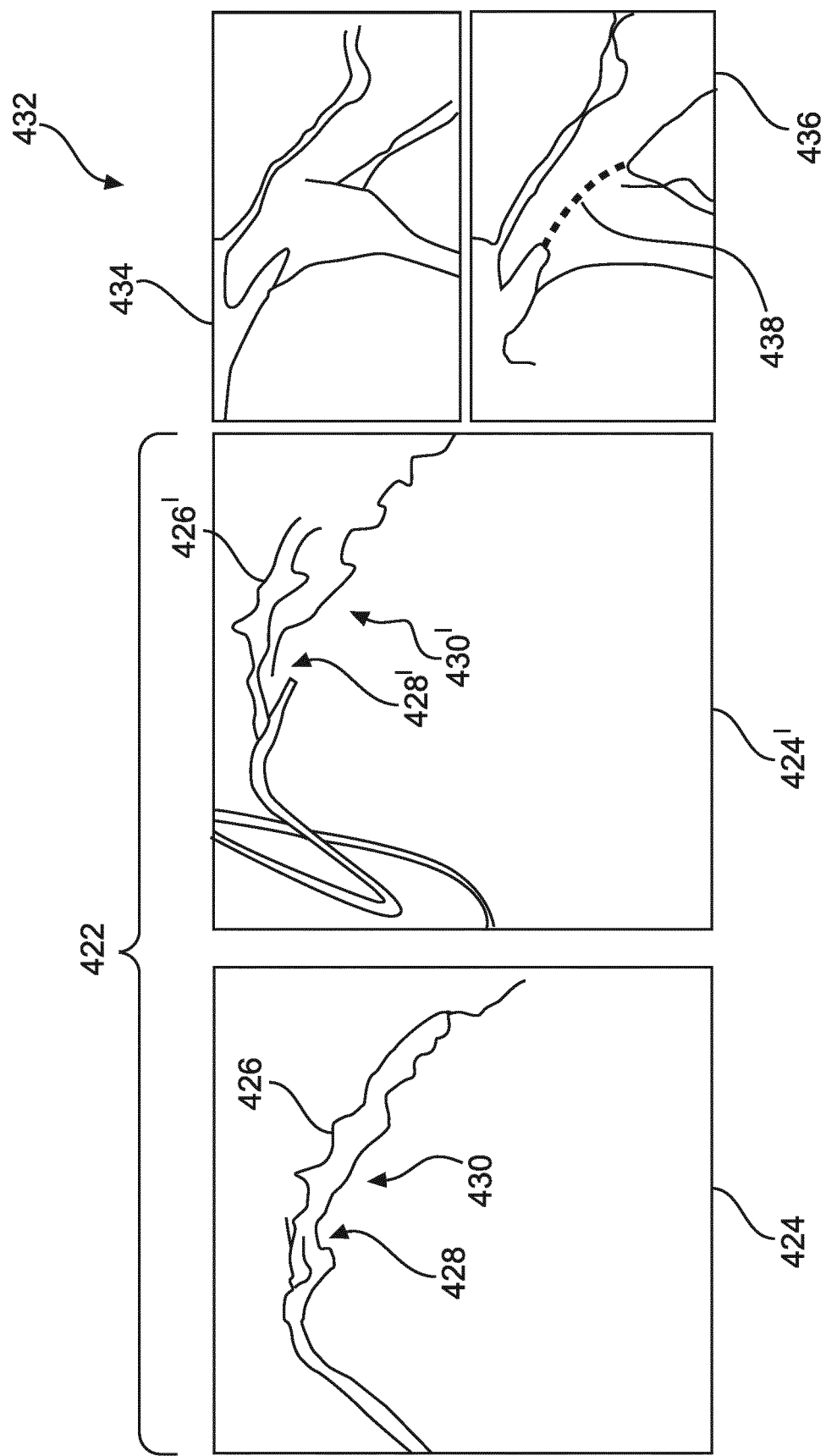
FIG. 8 shows angiograms of another example of a vascular structure with an occlusion and an indicated vessel course.

FIG. 8 relates to a second example of an occluded vessel. In a left part 422, two angiograms 424, 424' are shown with a second vascular structure 426, 426' having an occlusion 428, 428' where a distal part 430, 430' is faintly visible. In a right part 432, an upper image 434 shows an enlarged detailed view of the vascular structure 426', and a lower part 436 shows the detailed view with an interpolated vessel course 438.

Figure 9:
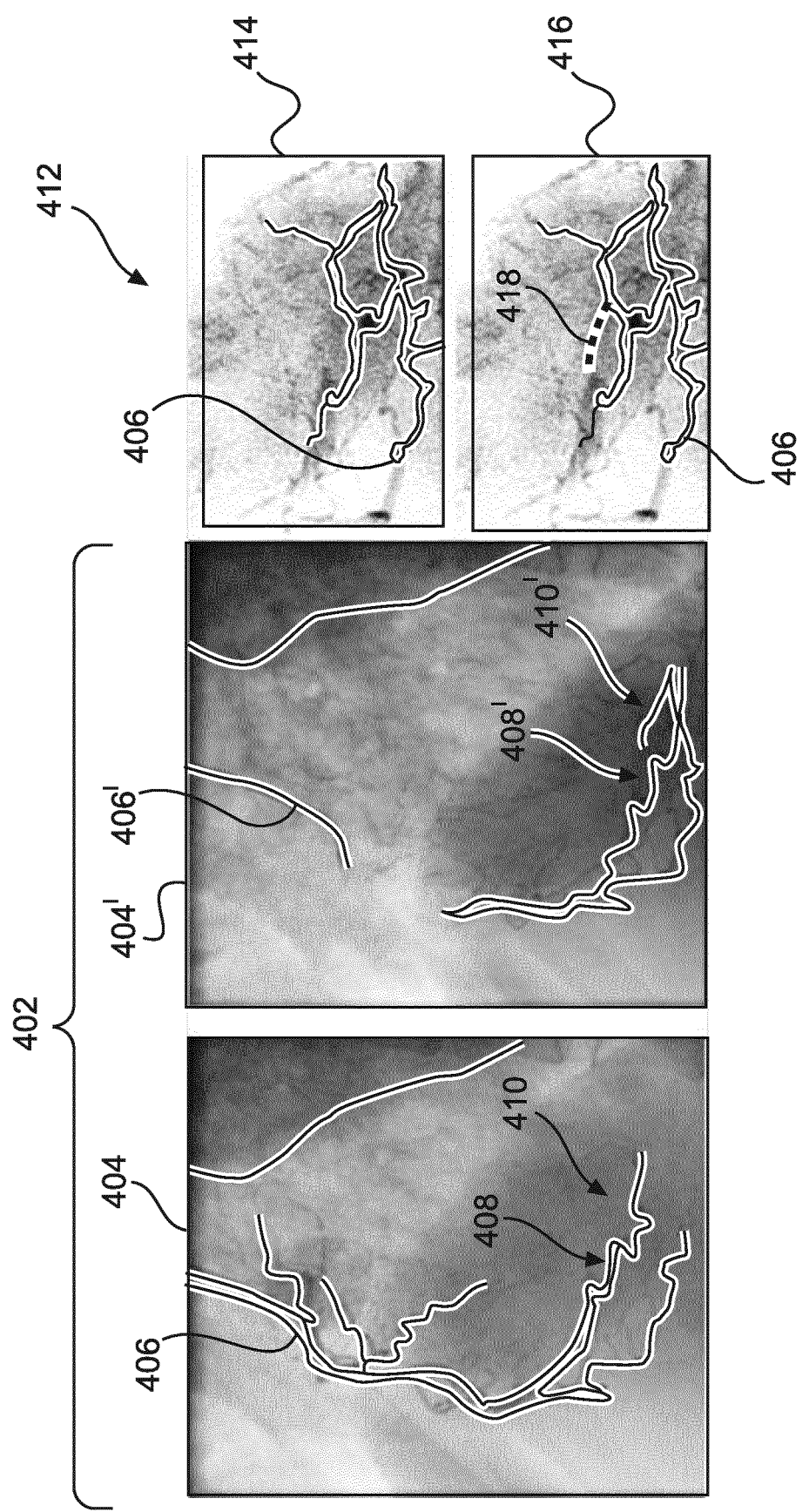
FIGS. 9 and 10 show the angiograms of FIGS. 7 and 8 as photographic illustrations.
Figure 10:
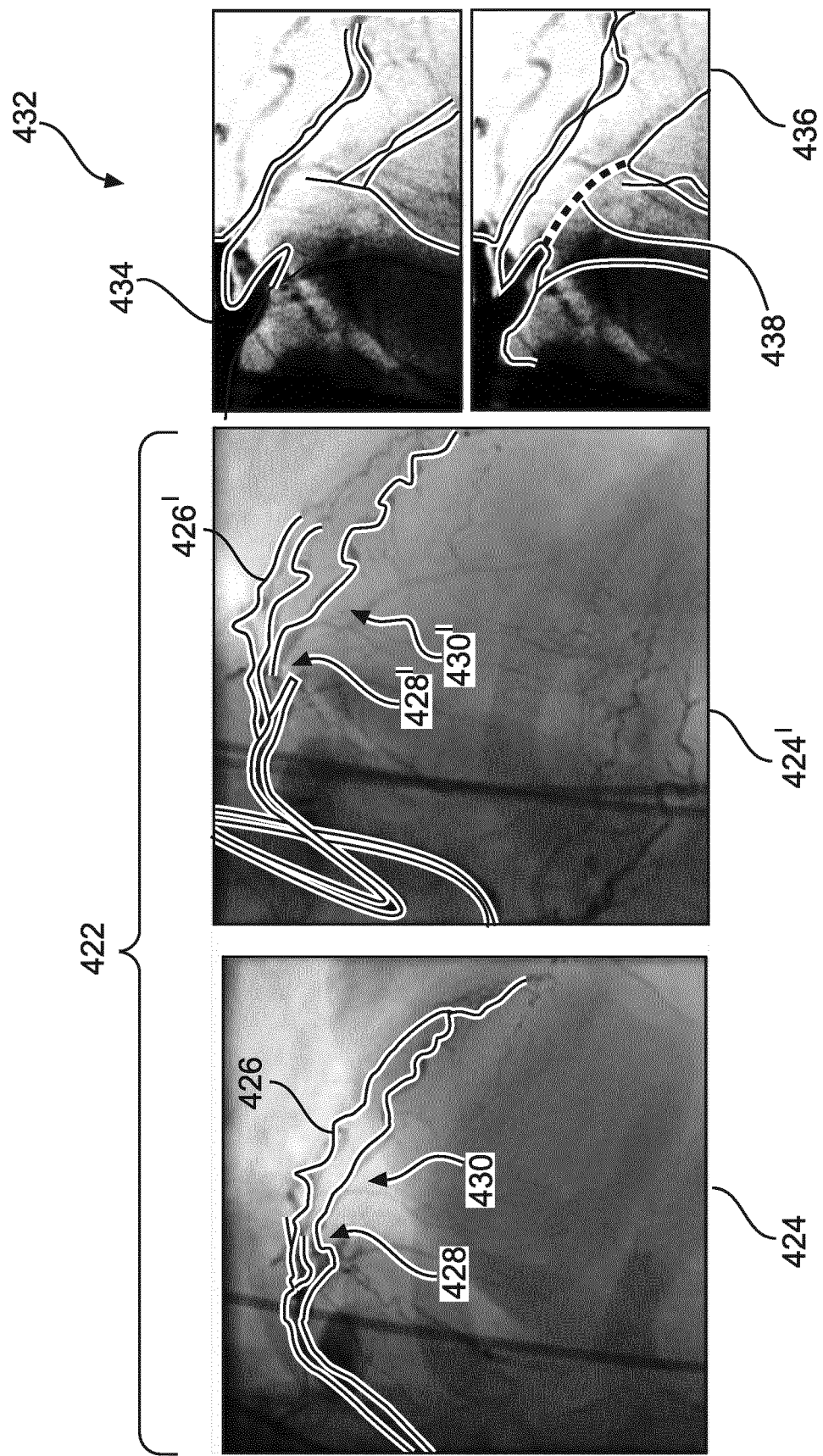

FIG. 9 shows a photographic illustration of FIG. 7; and FIG. 10 shows a photographic illustration of FIG. 8.

According to a first aspect, in an example, it is provided to semi-automatically define the most probable occluded vessel course, in the cases where the matching distal part is visible at some point of the angiographic sequence. The clinician sketches the vessel course he wants to follow in the intervention on one image; the system refines it and optionally extends it to the other heart phases, so that it is ready to use for (augmented) cardiac roadmapping.

In an example, in a first step, it is provided to refine the course drawn by the clinician so that it smoothly connects with the vessel parts proximal and distal to the occlusion. This step is desirable to allow for an edition from a touch-screen, where an accurate positioning cannot be expected. For each successive heart phase, many variations of the previous vessel course are considered, and the one that i) smoothly connects to the vessels proximal and distal to the occlusion and ii) follows an anatomically likely course, is selected. If different angiography images correspond to this heart phase, the trajectory presenting the best score regarding those two criteria is selected.

This process can be consolidated temporally, for instance by re-iterating it. It outputs one optimal trajectory for each heart phase.

The final result is reported over all the frames of the sequence, and on the corresponding roadmap. This yields an augmented roadmap that will accurately display, in real time and all along the heart cycle, where the trajectory targeted by the clinician lies.

In the course of the process, for each angiography frame it is associated a rough trajectory that corresponds to the estimated occluded vessel course. Initially, it may be the trajectory defined by the clinician on a selected image. Then, it is the trajectory selected on the previous heart phase.

To adapt it to the considered image (or to fine tune it for the initial frame), anatomically plausible variations of the input trajectory are generated, and evaluated for each one of them whether they smoothly connect to a distal vessel.

The best trajectory for each heart phase is selected. This scheme can be iterated for improved robustness.

Ultimately, it may be decided whether the set of proposed trajectories are of sufficient quality. If so, they are translated to each frame of the angiogram, or of the roadmap.

In an example, for the variation of the trajectory, it is provided: The input trajectory is first positioned at the location of the stump, by applying a global translation. This anchor point is automatically determined based on its resemblance to the (already identified) stump at the previous heart phase.

Then, the trajectory is modified around its initial shape to generate a (possible large range of) plausible trajectories matching the vessel course at the next heart phase. Each of these trajectories is associated an anatomical plausibility.

A simple way to achieve this is to add smooth variations to the original trajectory, for instance variations generated on a set of splines. The smallest the added variations, the highest the anatomical probability.

Another option is provided to learn, from a database of manually segmented vessel centerlines, the expected set of anatomical variations depending on the stump location (mid LAD/distal circumflex . . . ) and the angiographic viewing angle. A score would also be associated to each proposed trajectory as well.

In an example, for the evaluation of the (potential) connection with the vessel distal part, it is provided: If the vessel part distal to the occlusion is visible, some tested trajectories are expected to meet it. In particular, the real occluded vessel part should have a smooth course that nicely joins the proximal and distal part of the visible vasculature.

In that step, each trajectory is associated the stronger vessel contrast that it meets (over a given length). Since no perfect vessel map is expected to be available, it can be approximated as the strongest ridge met by the trajectory. A "ridge" refers to a kind of vessel energy obtained after filtering by a ridge filter (Frangi et al, MICCAI'98: "Multiscale vessel enhancement filtering") This indicator will tell how significant the crossed vasculature is; it will be close to zero if no such vasculature is met.

Additionally, it is evaluated whether the trajectory joins the (potential) distal vessel parallel to its course. Here again, it may be relied in practice on the ridge directions instead of the (unknown) segmented vasculature. A trajectory touching the distal vasculature with a strong (and thus unrealistic) angle will be strongly penalized.

In an example, for the selection of the best trajectory, it is provided: A composite score (the quality) is built that takes into account the previous indicators: anatomical likelihood, contrast of the distal vasculature, angle to distal vasculature. The trajectory that has the highest quality is selected.

Since the quality of a selected trajectory for one phase depends on the quality of the selected trajectory on the previous frame, this process can be re-iterated a number of times, for improved accuracy.

In an example, for the quality thresholding, it is provided: Since not every CTO case allows to see the distal part of the vessel, the interpolations can be so uncertain that it may be preferred not to show them to the clinician.

That decision can be made by thresholding the previously computed quality (summed over all the phases).

In an example, for the transfer to the complete sequence, it is provided: Starting from extrapolated good guesses of the vessel course in the occlusion for each heart phase, they can be associated to angiography images where the general vasculature is poorly visible.

This aims to translate the proposed course to every injected image of the same heart phase. In an example, a global translation is sufficient to model the motion to compensate for, since the heart is at the same exact contraction status.

In an example, the occlusion is positioned during the complete heart cycle at the location of the identified occlusion. In an option, it is refined to ensure an optimal smoothness at its connection with the stump. Alternatively, both images (the reference one with the vessel course, and the one considered for alignment) are aligned based on their vasculatures.

In an example, it is provided a potential manual edition. Since the invention is only a tool guessing the vessel course that does not rely on the (invisible) real lumen, the clinician is provided with the possibility to edit it, so that it best fits his intuition.

The visualization of the vasculature structures with an occlusion can be applied for CTO treatments in percutaneous coronary intervention (PCI).

As an example, the visualization is applied to C-arm based systems. The above examples provide support for a clinician, as it brings help in performing one of the most difficult PCI.

According to a second aspect, in an option, it is provided to automatically define the most probable occluded vessel course, in the cases where the matching distal part is visible at some point of the angiographic sequence. The (editable) result is displayed on the angiograms and roadmaps. This focuses on the neighborhood of the occlusion. The occlusion has either been manually given by the user, or has been detected automatically.

In an example, a series of possible prolongations of the stump are considered, frame by frame. They are associated a score depending on the contrast of the (potential) distal vasculature they meet, the smoothness of their connection to the vasculature proximally and distally, and their anatomical plausibility. Trajectories that do not meet any vasculature have the score "0" (zero).

A consolidated choice may be performed at the level of the angiographic sequence (as opposed to an independent frame by frame decision). It so-to-speak adds a fourth criterion that imposes successive trajectories to be similar. The final result is reported over all the frames of the sequence, and on the corresponding roadmap. In an option, the user is free to edit it, so that it better matches his clinical intuition.

In an example, for an identification of the branch distal to the occlusion, it is provided: This step can be performed automatically. The vasculature can be analyzed to detect vessels whose course stops abruptly. Alternatively, one could rely on the position of the guide wire during the intervention to determine at which point the clinician drives his tool, and tries to cross a non-injected region.

In an example, this step is performed manually. The clinician could roughly identify the region he is interested in by touching the corresponding area on an angiogram presented on a touch-pad.

In an example, for a generation of admissible vessel courses, it is provided: The identified occluded vessel branch is extended by virtually "throwing" possible vessel extensions originating from it. These extensions would have to smoothly connect to the stump, and follow plausible courses.

A way to achieve this is to extrapolate from the stump, starting a curve that fits the existing vessel, and prolonging it smoothly by means of splines for instance. The smoother the extension (the less it deviates from a straight line for instance), the more likely it is considered.

In another example, the processing unit learns from a database of manually segmented vessel centerlines, which courses are to be expected from a given initial vessel part. The proposed extensions are then different depending on the vessel part considered (mid LAD/distal circumflex . . . ) and the angiographic viewing angle. A score is associated to each proposed trajectory.

In an example, for an evaluation of the (potential) distal vessel part, it is provided: If the vessel part distal to the occlusion is visible, some tested trajectories are expected to meet it. In particular, the real occluded vessel part should have a smooth course that nicely joins the proximal and distal part of the visible vasculature. In that step, each trajectory is associated the stronger vessel contrast that it meets (over a given length). Since no perfect vessel map is expected to be available, it can be approximated as the strongest ridge met by the trajectory. This indicator will tell how significant the crossed vasculature is (and it will be close to zero if no such vasculature is met).

In a composite criterion, other criteria are also provided.

In an example, for a temporal consolidation, it is provided: The framework is now supposed to have processed each frame individually. For each frame, a list of trajectories is presented, associated with: an anatomical likelihood score; an evaluation of the significance of the distal vasculature it meets (contrast of the joined ridges); an evaluation of the smoothness of the connection to the distal vasculature (angle with the joined ridges).

The goal is to generate therefrom the most probable vessel course in the occlusion for each heart phase. In other words, for the most informative heart cycle, the most probable vessel courses are identified, while keeping these courses coherent.

This task can be performed systematically. For each tested heart cycle: i) The most probable vessel course associated to each heart phase is extracted (using the three indicators listed above). ii) A fourth indicator is computed penalizing the difference in the vessel courses between two different successive heart phases. iii) The most probable vessel course associated to each heart phase is extracted using the four indicators listed above. iv) An iteration is provided until convergence is achieved.

The best coherent courses can be selected for every possible heart cycle. They can also be associated with a quality measure, e.g. function of the four indicators listed above.

In another example, other criteria are added. For example, the "anatomical likelihood" is replaced by "the trajectory should be as close to a straight line as possible" or the like.

The proposed vessel courses for the cycle giving the highest quality is output.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for visualizing a course of an occluded vasculature, comprising:
   an image data supply circuit;
   a determination circuit;
   processing circuitry; and
   a display;
   wherein the image data supply circuit is configured to provide a sequence of images of a cardiac vasculature structure, which is at least partly injected with contrast agent;
   wherein the determination circuit is configured to determine a region of interest in a first image of the sequence of images of a cardiac vasculature structure;
   wherein the processing circuitry is configured to:
   i) identify, in the region of interest, a trajectory proposal from a first visible vessel portion proximal to a non-visible vessel portion of an occlusion to a second visible vessel portion distal to the non-visible vessel portion of the occlusion;
   ii) modify the trajectory proposal by generating a plurality of possible trajectories for matching with a vessel course of the non-visible vessel portion;
   iii) determine a plausibility value for at least one of the possible trajectories; and
   iv) select a possible trajectory for the vessel course based on the at least one plausibility value,
   wherein the display is configured to display an indication of the selected trajectory as the vessel course of the non-visible vessel portion in the cardiac vasculature structure.

2. The device according to claim 1, further comprising a user interface configured to provide manual identification or modification of image data.

3. The device according to claim 1, wherein the processing circuitry is configured to modify the trajectory proposal by generating several prolongations of the first visible portion of the vessel at the non-visible vessel portion as trajectory proposals.

4. The device according to claim 3, wherein the processing circuitry is configured to generate a score for each prolongation based on at least one of the group of:
   contrast for the potential distal vascular structure met by the prolongation,
   smoothness of their connection at the proximal and distal parts,
   anatomic probability for each prolongation, and
   similarity of successive trajectories,
      and select the prolongation based on the generated score.

5. The device according to claim 1, wherein the processing circuitry is configured to perform at least one of:
   associating a connection score to each of the possible trajectories based on a smoothness degree of the trajectory with visible portions of the vessel;
   associating an anatomical plausibility score to each of the possible trajectories based on a matching degree with an anatomical model of the vascular structure;
   associating an anatomical probability score based on a degree of variation of the possible trajectories with the selected trajectory for the previous image of the sequence;
   associating a matching score based on a degree of similarity with a number of vessel centerlines provided by a database; and
   associating a smoothness score based on a touching angle of the possible trajectories with a visible distal portion.

6. The device according to claim 1, wherein the processing circuitry is configured to modify the trajectory proposal by generating a plurality of possible trajectories for connecting the first visible vessel portion with the second visible vessel portion of the vessel, and wherein the processing circuitry is configured to associate an anatomical plausibility score to each of the possible trajectories based on a matching degree with an anatomical model of the vascular structure.

7. A method for visualizing a course of an occluded vasculature, comprising the following steps:
   a) determining a region of interest in a first image of a sequence of images of a cardiac vasculature structure, which is at least partly injected with contrast agent;
   b) identifying, in the region of interest, a trajectory proposal from a first visible vessel portion proximal to a non-visible vessel portion of an occlusion to a second visible vessel portion distal to the non-visible vessel portion of the occlusion;
   c) modifying the trajectory proposal by generating a plurality of possible trajectories for matching with a vessel course of the non-visible vessel portion;
   d) determining a plausibility value for at least one of the possible trajectories;
   e) selecting a possible trajectory for the vessel course based on the at least one plausibility value;
   h) indicating the selected trajectory as the vessel course of the non-visible vessel portion in the cardiac vasculature structure.

8. The method according to claim 7, further comprising the steps of:
   f) repeating steps c) to e) for each image of the sequence to achieve a sequence of vessel course indicators; and
   g) associating the vessel course indicators to the images corresponding to the same heart phase of the sequence of the cardiac vasculature structure.

9. The method according to claim 7:
   wherein, in step a), a vessel branch distal to an occlusion is determined automatically; and wherein, preferably, vessels are detected that stop abruptly.

10. The method according to claim 7, wherein, in step b), the trajectory is manually identified by a user via an interface.

11. The method according to claim 7, wherein, in step b), the trajectory is identified automatically.

12. The method according to claim 7, wherein, for step c), several prolongations of the first visible portion at the non-visible vessel portion are provided as trajectory proposals.

13. The method according to claim 12, wherein, in step d), a score is provided for each prolongation based on at least one of the group of:
   contrast for the potential distal vascular structure met by the prolongation,
   smoothness of their connection at the proximal and distal parts,
   anatomic probability for each prolongation, and
   similarity of successive trajectories,
      and step e) comprises selecting the prolongation based on the score.

14. The method according to claim 7, wherein, following step b), refining the trajectory proposal input by a user in order to correct for input inaccuracy; and
   wherein the refinement includes smoothening the connecting parts of the trajectory proposal where a connecting with visible vessel portions is provided.

15. The method according to claim 7, wherein step d) comprises at least one of the following sub-steps:
   d1) associating a connection score to each of the possible trajectories based on a smoothness degree of the trajectory with visible portions of the vessel;
   d2) associating an anatomical plausibility score to each of the possible trajectories based on a matching degree with an anatomical model of the vascular structure;
   d3) associating an anatomical probability score based on a degree of variation of the possible trajectories with the selected trajectory for the previous image of the sequence;
   d4) associating a matching score based on a degree of similarity with a number of vessel centerlines provided by a database; and
   d5) associating a smoothness score based on a touching angle of the possible trajectories with a visible distal portion.

16. The method according to claim 7, wherein, in step e), a trajectory is selected for each heart phase.

17. The method according to claim 7, wherein step e) comprises a sub-step e1) of manually modifying the possible trajectory by the user via an interface.

18. The method according to claim 7, wherein modifying the trajectory proposal comprises generating a plurality of possible trajectories for connecting the first visible vessel portion with the second visible vessel portion of the vessel, and wherein determining a plausibility value comprises associating an anatomical plausibility score to each of the possible trajectories based on a matching degree with an anatomical model of the vascular structure.

19. A non-transitory computer-readable storage medium having stored therein instructions that when executed by processing circuitry are configured to control a device for visualizing a course of an occluded vasculature, by providing a sequence of images of a cardiac vasculature structure, which is at least partly injected with contrast agent;

determining a region of interest in a first image of the sequence of a cardiac vasculature structure;

identifying in the region of interest, a trajectory proposal from a first visible vessel portion proximal to a non-visible vessel portion to a second visible vessel portion distal to the non-visible vessel portion of an occlusion;

modifying the trajectory proposal by generating a plurality of possible trajectories for matching with a vessel course of the non-visible vessel portion;

determining a plausibility value for at least one of the possible trajectories;

selecting a possible trajectory for the vessel course based on the plausibility value of the trajectory, displaying an indication of the selected trajectory as the vessel course of the non-visible vessel portion in the cardiac vasculature structure.

* * * * *